United States Patent
Tsuchida

(10) Patent No.: US 6,537,933 B1
(45) Date of Patent: Mar. 25, 2003

(54) SILK CLOTHS FOR PROTECTING AFFECTED PARTS

(76) Inventor: Yuzo Tsuchida, 15-7, Koyama 4-chome, Shinagawa-ku, Tokyo 142-0062 (JP)

( * ) Notice: Subject to any disclaimer, the term of this patent is extended or adjusted under 35 U.S.C. 154(b) by 0 days.

(21) Appl. No.: 09/701,487

(22) PCT Filed: Jun. 1, 1999

(86) PCT No.: PCT/JP99/02905

§ 371 (c)(1),
(2), (4) Date: Nov. 29, 2000

(87) PCT Pub. No.: WO99/62444

PCT Pub. Date: Dec. 9, 1999

(30) Foreign Application Priority Data

Feb. 17, 1999 (JP) .......................... 11-039112

(51) Int. Cl.[7] .............................. B32B 27/04
(52) U.S. Cl. ................ 442/123; 442/152; 442/268; 442/319; 442/381; 428/364; 428/365; 106/15.05; 106/402; 106/404; 106/405; 602/43; 602/44; 602/45; 602/76
(58) Field of Search ................ 442/123, 152, 442/268, 319, 381; 428/357, 364, 365, 375; 106/15.05; 424/78.07, 400, 402, 404, 405, 443, 445; 510/130, 131; 602/41, 42, 43, 44, 45, 75, 76; 604/304, 307

(56) References Cited

U.S. PATENT DOCUMENTS

| | | | | | |
|---|---|---|---|---|---|
| 3,895,474 | A | * | 7/1975 | Bauer | 53/21 |
| 4,891,228 | A | * | 1/1990 | Thaman et al. | 424/443 |
| 5,358,714 | A | * | 10/1994 | Green | 424/400 |
| 5,525,340 | A | * | 6/1996 | Fukunaga | 424/195.1 |
| 5,741,553 | A | * | 4/1998 | Manolas et al. | 427/421 |
| 5,908,707 | A | * | 6/1999 | Cabell et al. | 428/537.5 |
| 6,190,678 | B1 | * | 2/2001 | Hasenoehrl et al. | 424/401 |
| 6,258,368 | B1 | * | 7/2001 | Beerse et al. | 424/404 |
| 6,287,583 | B1 | * | 9/2001 | Warren et al. | 424/404 |

FOREIGN PATENT DOCUMENTS

| | | |
|---|---|---|
| JP | A092960 | 1/1997 |
| JP | 3040661 | 6/1997 |

* cited by examiner

Primary Examiner—Elizabeth M. Cole
Assistant Examiner—Ula C. Ruddock
(74) Attorney, Agent, or Firm—Birch, Stewart, Kolasch & Birch, LLP

(57) ABSTRACT

Silk clothes for protecting affected parts (incised wound, burn, tumor, bedsore, etc.) which also contribute to the prevention of suppurating. These clothes are composed of a knitted woven silk fabric or non-woven silk fabric (silk floss, etc.) containing either *Sasa veitchii* or a parabenzoic acid ester or both of the same and being adhered to a non-woven fabric made of cellulose, etc.

7 Claims, 1 Drawing Sheet

SILK CLOTHS FOR PROTECTING AFFECTED PARTS

This application is the national phase under 35 U.S.C. §371 of PCT International Application No. PCT/JP99/02905 which has an International filing date of Jun. 1, 1999, which designated the United States of America.

BACKGROUND AND SUMMARY OF THE INVENTION

2. Technical Field

The present invention relates to protective silk cloths, adapted to be applied to affected body parts, such as cuts, burns, tumors, bedsores, and the like, to protect such affected parts.

2. Background Technology

Protecting affected parts with protective silk cloths is known to the public by means of Utility Model Registration Nos. 3,040,123 and 3,040,661 that were devised by the inventor of the present patent application.

Conventional protective silk cloths of the prior art have the feature of not causing a patient to feel self conscious with their use because of excellent conformability of silk itself to the skin, and because of virulence absorbability of silk which absorbs substances detrimental to cure, such as humidity, suppuration, direct, and the like, thereby contributing to improvement in the curing effects of affected parts. However, because of a lack of antibacterial properties, such protective silk cloths are likely to cause suppuration in the affected body parts, such as cuts, burns, bedsores, and the like, unless treatment, such as applying an antibacterial agent and the like, is separately provided to the affected body parts.

The present invention is made to solve the problem described above. Thus, an object of the present invention is to provide a protective silk cloth having antibacterial properties.

DISCLOSURE OF THE INVENTION

In order to achieve the object described above, the present invention provides a protective cloth for affected body parts, comprising a piece of silk fabric containing an extract of *Sasa veitchii* (Carriere) Rehder (common name); Kumazasa) (hereinafter referred to as "*Sasa veitchii*") that has antibacterial properties and/or an antibacterial agent, such as a parabenzoic ester, and the like.

The silk fabric may be knitted or woven fabric made by knitting or weaving raw silk or spun silk yarn, or non-woven fabric made by twisting floss silk, or the like, into a fabric-like texture. The protective silk cloth for affected body pars may also comprise a piece of this silk fabric, such as floss silk, or the like, adhered by means of adhesive, to a piece of non-woven fabric made of either cellulose (produced from wooden pulp, or the like), a polyester, a polyurethane, or the like, or to a piece of non-woven fabric made of cellulose, reinforced with a polyurethane or the like.

For the parabenzoic ester, a solution may be used of either n-butyl-p-hydroxybenzoic acid or n-propyl-p-hydroxybenzoic acid, both well known as an antibacterial agent, mixed with an alcohol, such as ethanol.

For *Sasa veitchii* extract, a *Sasa veitchii* extract may be used as an agent having antibacterial properties when applied to affected body parts, such as burns, and the like.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Best Embodiments of the Invention

Figure 1:
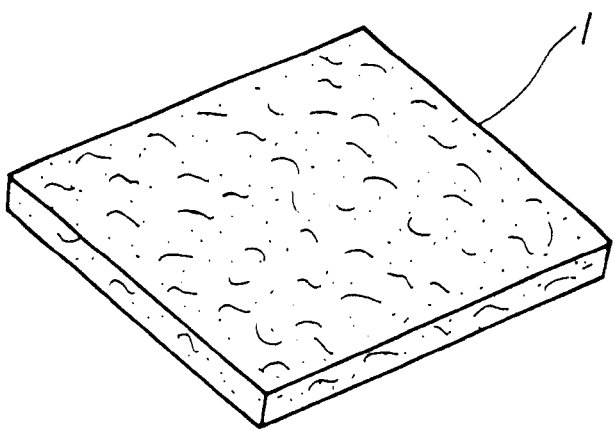
FIG. 1 is a perspective view of a protective cloth, according to the present invention.
Figure 2:
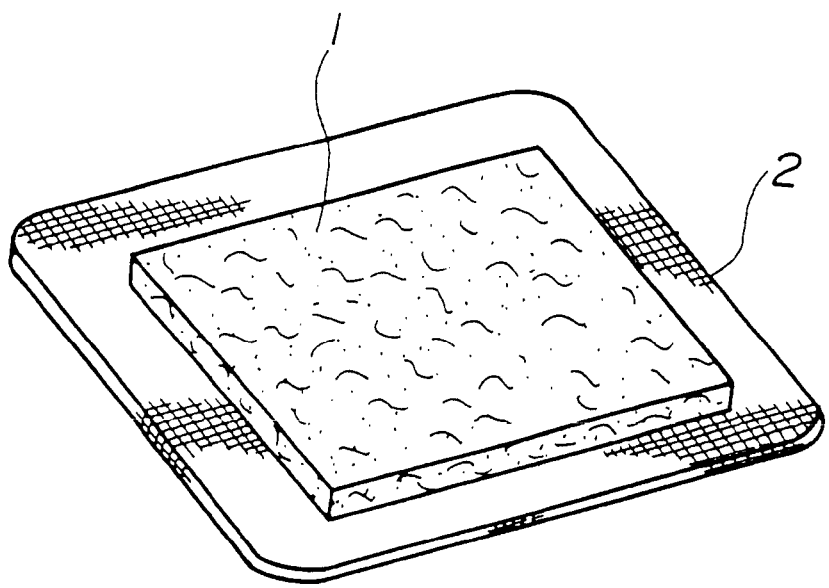
FIG. 2 is a perspective view of a protective cloth adhered to a piece of non-woven fabric, according to the present invention.

As shown in FIG. 1, a protective cloth, according to the present invention, may be manufactured by spraying the cloth with *Sasa veitchii* extract, and/or an alcoholic solution of parabenzoic ester, and then drying the composite, the cloth being a piece of silk fabric 1 of floss silk, or the like, or by impregnating the cloth with *Sasa veitchii* extract and/or an alcoholic solution of parabenzoic ester, and then drying the composite. Also, as shown in FIG. 2, if required, the protective cloth, according to the present invention, may be manufactured by adhering a piece of silk fabric 1, to a piece of non-woven fabric 2 made of either cellulose (produced from wooden pulp, or the like), a polyester, or a polyurethane, or to a piece of non-woven fabric 2 made of cellulose reinforced with polyurethane, or the like.

In addition to the conformability to the skin and the absorbability of the silk itself, a protective cloth manufactured as described above contains one or more from *Sasa veitchii* extract, that used to be applied as an agent having antibacterial properties from the old times, and parabenzoic esters, well known as antibacterial agents, thereby equipping the silk with antibacterial properties which are useful for preventing affected body parts form suppurating.

These protective cloths, mainly made of such natural materials, and protective cloths, made of synthetic materials not including vinyl chloride, are inexpensive and, furthermore, are capable of being disposed as waste without causing environmental pollution.

As described above, in addition to the conformability to the skin and the virulence absorbability for absorbing humidity, suppuration, and the like, of silk itself, the protective silk cloth according to the present invention exhibits especially strong antibacterial properties against *Pseudomonas aeruginosa*, due to agents such as *Sasa veitchii* extract and parabenzoic esters, contained therein. Thus, excellent effects are obtained in that the protective silk cloths, according to the present invention, are not only effective against affected body parts, such as tumors, having inflammation, but are also useful for preventing the affected body parts, such as cuts, burns, bedsores, and the like, from suppurating.

Next, the present invention will be discussed based on antibacterialness tests.

In the tests, sample floss silk is cut out to obtain circular disks of about a 2-cm diameter, which are then put in respective Petri dishes separately, as specimens. After test bacteria solution of 0.1 ml (milliliter) is dripped on the testing surface of each specimen, each dish has its cover secured and is preserved for 19 hours under the conditions of 35 degrees C. (deg.C.) temperature and 90% relative humidity. After the preservation, each specimen is washed out using sterile, physiological salt solution of 1.9 ml, to obtain a recovery solution. With the recovery solution, the number of live bacteria is measured by means of the agar plating method (cultivation for 24 hours at 35 deg.C.) using normal agar. In case no bacteria are detected, the number of bacteria after preservation is denoted as "<50."

Test bacteria solution described herein is obtained by transplanting test bacteria to an SCD cultivation medium for subsequent precultivation for nine hours at 35 deg.C., and thereafter diluting the precultivation solution with sterile, physiological salt solution so as to obtain the number of bacteria equal to $10^5$/ml.

[Illustrative Embodiment 1 (*Escherichia coli*)]

As shown in Table 1, floss silk was soaked in five different types of test solutions, respectively, and dried after the soaking, to obtain Specimens No.1–No.5. Untreated floss silk was denoted as Specimen No.6.

TABLE 1

| Specimen | Test Solution |
|---|---|
| No. 1 | *Sasa veitchii* extract; |
| No. 2 | Ethanol containing n-butyl-p-hydroxybenzoic acid by 10% (also referred to as 10%-butyl-parabenzoic-ester ethanol); |
| No. 3 | Ethanol containing n-butyl-p-hydroxybenzoic acid by 20% (also referred to as 20%-butyl-parabenzoic-ester ethanol); |
| No. 4 | Ethanol containing n-propyl-p-hydroxybenzoic acid by 10% (also referred to as 10%-propyl-parabenzoic-ester ethanol); |
| No. 5 | Ethanol containing n-propyl-p-hydroxybenzoic acid by 20% (also referred to as 20%-propyl-parabenzoic-ester ethanol); and |
| No. 6 | Untreated. |

Antibacterialness tests were applied to each specimen by means of *Escherichia coli* (*Escherichia coli* IFO 3972) to obtain a result as shown in Table 2.

TABLE 2

A Result of Measuring the Number of Live Bacteria

| Specimen | (Test Solution) | A | B |
|---|---|---|---|
| No. 1 | (*Sasa veitchii* extract) | $4.60 \times 10^5$ | <50 |
| No. 2 | (10%-butyl-parabenzoic-ester ethanol) | Same | $8.0 \times 10^5$ |
| No. 3 | (20%-butyl-parabenzoic-ester ethanol) | Same | <50 |
| No. 4 | (10%-propyl-parabenzoic-ester ethanol) | Same | <50 |
| No. 5 | (20%-propyl-parabenzooic-ester ethanol) | Same | <50 |
| No. 6 | (Untreated) | Same | $3.30 \times 10^5$ |

(where A and B denote the number of inocula bacteria and the number of bacteria after preservation, respectively.)

From Table 2, it was confirmed that Specimens Nos. 1, 3, 4 and 5, containing *Sasa veitchii* extract, 20%-butyl-parabenzoic-ester ethanol, and 10%- and 20%-propyl-parabenzoic-ester ethanol, respectively, exhibited sufficient antibacterialness against *Escherichia coli*. However, both Specimen No.2 that contained 10%-butyl-parabenzoic-ester ethanol, and Specimen No.6 that was untreated, did not show sufficient antibacterialness against *Escherichia coli*.

[Illustrative Embodiment 2 (*Pseudomonas aeruginos*)]

As shown in Table 3, Specimen No.7 was obtained by having floss silk soaked in a 1-in-6 diluted *Sasa veitchii* extract, and dried after the soaking, with Specimen No.8 obtained by having Specimen No.7 further gas sterilized, while Specimen No.9 was obtained by having floss silk soaked in a mixture solution in equivalent ratios of a 1%-butyl-parabenzoic-ester-containing ethanol and a 1-in-10 diluted *Sasa veitchii* extract, and dried after the soaking. Untreated floss silk was denoted as Specimen No. 10.

TABLE 3

| Specimen | Test Solution |
|---|---|
| No. 7 | 1-in-6 diluted *Sasa veitchii* extract; |
| No. 8 | 1-in-6 diluted *Sasa veitchii* extract, gas sterilized |

TABLE 3-continued

| Specimen | Test Solution |
|---|---|
| No. 9 | Mixture solution; and |
| No. 10 | Untreated. |

Antibacterialness tests were applied to these specimens by means of *Pseudomonas aeruginos* (*Pseudomonas aeruginos* IFO 13275) to obtain a result as shown in Table 4.

TABLE 4

| Specimen | (Test Solution) | A | B |
|---|---|---|---|
| No. 7 | (1-in-6 diluted *Sasa veitchii* extract) | $8.10 \times 10^5$ | <50 |
| No. 8 | (No. 7 Test Solution, further gas sterilized) | Same | <50 |
| No. 9 | (Mixture solution) | Same | <50 |
| No. 10 | (Untreated) | Same | $1.90 \times 10^7$ |

(where A and B denote the number of inocula bacteria and the number of bacteria after preservation, respectively.)

Table 4 confirms that Specimens Nos. 7 and 8, containing the 1-in-6 diluted *Sasa veitchii* extract, and Specimen No.9, containing the mixture solution of the 1-in-10 diluted *Sasa veitchii* extract and the 1%-butyl-parabenzoic-ester-containing ethanol, respectively, exhibited sufficient antibacterialness against *Pseudomonas aeruginos*, where no significant differences were found in the antibacterialness between Specimen No.7, which was made to contain the 1-in-6 diluted *Sasa veitchii* extract and just dried thereafter, and Specimen No.8, which was obtained by further gas sterilizing such Specimen No.7. However, Specimen No.10 that was untreated, did not show antibacterialness against *Pseudomonas aeruginos*.

[Illustrative Embodiment 3 (*Staphylococcus aureus*)]

As shown in Table 5, Specimen No.11 was obtained by having floss silk soaked in a 1-in-6 diluted *Sasa veitchii* extract, and dried after the soaking, with Specimen No.12 obtained by having Specimen No.11 further gas sterilized, while Specimen No.13 was obtained by having floss silk soaked in a mixture solution in equivalent ratios of a 1%-butyl-parabenzoic-ester-containing ethanol and a 1-in-10 diluted *Sasa veitchii* extract, and dried after the soaking. Untreated floss silk was denoted as Specimen No.14.

TABLE 5

| Specimen | Test Solution |
|---|---|
| No. 11 | 1-in-6 diluted *Sasa veitchii* extract; |
| No. 12 | 1-in-6 diluted *Sasa veitchii* extract, gas sterilized; |
| No. 13 | Mixture solution; and |
| No. 14 | Untreated. |

Antibacterialness tests were applied to these specimens by means of *Staphylococcus aureus* (*Staphylococcus aureus* IFO 12732) to obtain a result as shown in Table 6.

TABLE 6

| Specimen | (Test Solution) | A | B |
|---|---|---|---|
| No. 11 | (1-in-6 diluted *Sasa veitchii* extract) | $4.00 \times 10^5$ | <50 |
| No. 12 | (No. 7 Test Solution) (further gas sterilized) | Same | $9.6 \times 10^3$ |
| No. 13 | (Mixture solution) | Same | <50 |
| No. 14 | (Untreated) | Same | $8.70 \times 10^5$ |

(where A and B denote the number of inocula bacteria and the number of bacteria after preservation, respectively.)

From Table 6, it was confirmed that Specimen No.11 containing the 1-in-6 diluted *Sasa veitchii* extract, and Specimen No.13, containing the mixture solution of the 1-in-10 diluted *Sasa veitchii* extract and the 1%-butyl-parabenzoic-ester-containing ethanol, respectively, exhibited strong antibacterialness against *Staphylococcus aureus*, while Specimen No.12 that was obtained by gas sterilizing floss silk containing the 1-in-10 diluted *Sasa veitchii* extract, was inferior in antibacterialness against *Staphylococcus aureus* than Specimen No.11 that was not gas sterilized. Specimen No.14 that was untreated, did not show antibacterialness against *Staphylococcus aureus*.

[Illustrative Embodiment 4 (*Escherichia coli*)]

As shown in Table 7, Specimen No.15 was obtained by having floss silk soaked in a 1-in-6 diluted *Sasa veitchii* extract, and dried after the soaking, with Specimen No.16 obtained by having Specimen No. 15 further gas sterilized, while Specimen No.17 was obtained by having floss silk soaked in a mixture solution in equivalent ratios of a 1%-butyl-parabenzoic-ester-containing ethanol and a 1-in-10 diluted *Sasa veitchii* extract, and dried after the soaking. Untreated floss silk was denoted as Specimen No. 18.

TABLE 7

| Specimen | Test Solution |
| --- | --- |
| No. 15 | 1-in-6 diluted *Sasa veitchii* extract; |
| No. 16 | 1-in-6 diluted *Sasa veitchii* extract, gas sterilized; |
| No. 17 | Mixture solution; and |
| No. 18 | Untreated. |

Antibacterialness tests were applied to these specimens by means of *Staphylococcus aureus* (*Escherichia coli* IFO 3972) to obtain a result as shown in Table 8.

TABLE 8

| Specimen | (Test Solution) | A | B |
| --- | --- | --- | --- |
| No. 15 | (1-in-6 diluted *Sasa veitchii* extract) | $1.10 \times 10^5$ | $9.50 \times 10^4$ |
| No. 16 | (No. 7 Test Solution) (further gas sterilized) . . . | Same | $9.00 \times 10^4$ |
| No. 17 | (Mixture solution) | Same | <50 |
| No. 18 | (Untreated) | Same | $1.60 \times 10^6$ |

From Table 8, it was confirmed that Specimen No.17, containing the mixture solution of the 1-in-10 diluted *Sasa veitchii* extract and the 1%-butyl-parabenzoic-ester-containing ethanol, exhibited strong antibacterialness against *Escherichia coli*. However, Specimen No.15, containing the 1-in-6 diluted *Sasa veitchii* extract, and Specimen No.16, obtained by having Specimen No.15 further gas sterilized, were not that strong, but in a range of slightly stronger than the untreated Specimen 18, in terms of antibacterialness against *Escherichia coli*.

It is noted that the tests with the 1-in-6 diluted *Sasa veitchii* extract has revealed a phenomenon that *Sasa veitchii* extract reacts strongly to strong bacteria, such as *Pseudomonas aeruginosa*, but reacts weakly to bacteria that are weak and necessary to an extent, such as *Escherichia coli*. Thus, it can be said that *Sasa veitchii* extract is best and ideal for use in sticking plaster, and the like.

What is claimed is:

1. A silk cloth for protecting affected body parts, comprising a piece of knitted or woven silk fabric or non-woven silk fabric containing *Sasa veitchii* extract or a mixture of *Sasa veitchii* extract and parabenzoic ester.

2. A silk cloth for protecting affected body parts, according to claim 1, wherein said parabenzoic ester is mixed with ethanol.

3. The silk cloth for protecting affected body parts, according to claim 2, wherein said parabenzoic ester is n-butyl-p-hydroxybenzoic acid or n-propyl-p-hydroxybenzoic acid, or a mixture thereof.

4. A silk cloth for protecting affected body parts, comprising a piece of silk cloth impregnated with *Sasa veitchii* extract or a mixture of *Sasa veitchii* extract with ethanol containing at least 20% of n-butyl-p-hydroxybenzoic acid or ethanol containing at least 10% of n-propyl-p-hydroxybenzoic acid.

5. A silk cloth for protecting affected body parts, according to claim 4, wherein said piece of silk cloth is adhered to a piece of non-woven fabric made of either a cellulose, a polyester, a polyurethane or to a piece of non-woven fabric made of cellulose, reinforced with a polyurethane.

6. A silk cloth for protecting affected body parts, comprising a piece of cloth silk impregnated with either *Sasa veitchii* extract or a mixture of *Sasa veitchii* extract with ethanol containing parabenzoic ester.

7. A silk cloth for protecting affected body parts, according to claim 6, wherein said piece of silk cloth is adhered to a piece of non-woven fabric made of either cellulose, a polyester, a polyurethane, or to a piece of non-woven fabric made of cellulose, reinforced with a polyurethane.

* * * * *